(12) United States Patent
Giuliani et al.

(10) Patent No.: US 8,785,399 B2
(45) Date of Patent: Jul. 22, 2014

(54) ANTIBACTERIAL PEPTIDES

(75) Inventors: Andrea Giuliani, Biella (IT); Giovanna Pirri, Biella (IT); Silvia Fabiole Nicoletto, Biella (IT)

(73) Assignee: Spiderbiotech S.R.A., Colleretto Giacosa (IT)

( * ) Notice: Subject to any disclaimer, the term of this patent is extended or adjusted under 35 U.S.C. 154(b) by 632 days.

(21) Appl. No.: 12/995,802

(22) PCT Filed: Jun. 2, 2009

(86) PCT No.: PCT/EP2009/003931
§ 371 (c)(1),
(2), (4) Date: Dec. 2, 2010

(87) PCT Pub. No.: WO2009/146886
PCT Pub. Date: Dec. 10, 2009

(65) Prior Publication Data
US 2011/0077192 A1     Mar. 31, 2011

Related U.S. Application Data

(60) Provisional application No. 61/058,010, filed on Jun. 2, 2008.

(51) Int. Cl.
*C07K 14/00* (2006.01)
*A61K 38/16* (2006.01)
*A61K 38/08* (2006.01)
*A01N 25/00* (2006.01)

(52) U.S. Cl.
USPC .......... 514/21.3; 514/21.6; 530/324; 424/404

(58) Field of Classification Search
None
See application file for complete search history.

(56) References Cited

U.S. PATENT DOCUMENTS 8,268,961 B2 * 9/2012 Bracci et al. .................. 530/328

FOREIGN PATENT DOCUMENTS

| IT | WO-2006/006195 | * | 1/2006 |
| WO | WO 2006/006195 A1 | | 1/2006 |
| WO | WO 2006/050611 A1 | | 5/2006 |
| WO | WO 2008/022444 A1 | | 2/2008 |

OTHER PUBLICATIONS

Frecer, "QSAR Analysis of Antimicrobial and Haemolytic Effects of Cyclic Cationic Antimicrobial Peptides Derived from Protegrin-1," Bioorganic & Medicinal Chemistry, 2006, vol. 14(17):6065-6074.

Pini et al., "Antimicrobial Activity of Novel Dendrimeric Peptides Obtained by Phage Display Selection and Rational Modification," Antimicrobial, Agents and Chemotherap, 2005, vol. 19(7):2665-2672.
Pini et al., "Characterization of the Branched Antimicrobial Peptide M6 by Analyzing its Mechanisms of Action and In Vivo Toxicity," 2007, vol. 13(8):393-399.
International Search Report for PCT/EP2009/003931 dated Dec. 29, 2009 (2 pages).
Chin et al., 2007, "Antimicrobial Activities of Ceragenins Against Clinical Isolates of Resistant *Staphylococcus aureus*," Antimicrobial Agents and Chemotherapy, 51(4):1268-1273.
Del Pozo et al., 2007, "The Challenge of Treating Biofilm-Associated Bacterial Infections," Clinical Pharmacology & Therapeutics, 82(2):204-209.
Durr et al., 2006, "LL-37, The Only Human Member of the Cathelicidin Family of Antimicrobial Peptides," Biochimica et Biophysica Acta. 1758:1408-1425.
Gordon et al., 2005, "A Review of Antimicrobial Peptides and Their Therapeutic Potential as Anti-Infective Drugs," Curr. Eye. Res., 30(7):505-515.
Hancock et al., 1998, "Cationic Peptides: A New Source of Antibiotics," Tibtech, 16:82-88.
Irwin, 1968, "Comprehensive Observational Assessment: la. A Systematic, Quantitative Procedure for Assessing the Behavioral and Physiologic State of the Mouse," Psychopharmacologia (Berl.) 13:222-257.
Lehrer et al., 1999, "Antimicrobial Peptides in Mammalian and Insect Host Defence," Current Opinion in Immunology, 11:23-27.
Marr et al., 2006, "Antibacterial Peptides for Therapeutic Use: Obstacles and Realistic Outlook," Current Opionion in Pharmacology, 6:468-472.
Radek et al., 2007, "Antimicrobial Peptides: Natural Effectors of teh Innate Immune System," Semin Immunopathol, 29:27-43.
Radzishevsky et al., 2007, "Improved Antimicrobial Peptides Based on Acyl-Lysine Oligomers," Nature Biotechnology, 25(6):657-659.
Scott et al., 1999, "Biological Properties of Structurally Related alpha-Helical Cationic Antimicrobial Peptides," Infection and Immunity, 67(4):2005-2009.
Shin et al., 2007, "Structure-Antibacterial, Antitumor and Hemolytic Activity Relationships of Cecropin A-Magainin 2 and Cecropin A-Melittin Hybrid Peptides," The Journal of Peptide Research, 53: 82-90.
National Committee for Clinical Laboratory Standards, 2007, "Methods for Dilution Antimicrobial Susceptibility Tests for Bacteria That Grow Aerobically; Approved Standard—Seventh Edition," NCCLS document M7-A7, NCCLS, Wayne, PA. 2006.

* cited by examiner

*Primary Examiner* — Satyanarayana R Gudibande
(74) *Attorney, Agent, or Firm* — Sutherland Asbill & Brennan LLP

(57) ABSTRACT

The present invention relates to monomeric and multimeric peptidic compounds which have antimicrobial activity, particularly against Gram-positive and Gram-negative bacteria. Further, the present invention refers to compositions comprising said peptidic compounds for medical use, for use as a disinfectant and/or detergent or for use as a preservative.

30 Claims, 3 Drawing Sheets

ANTIBACTERIAL PEPTIDES

CROSS REFERENCE TO RELATED APPLICATIONS

This application claims the priority benefit of PCT/EP2009/003931 filed on Jun. 2, 2009 and U.S. Provisional application Ser. No. 61/058,010 filed on Jun. 2, 2008. The entire contents of these applications are hereby incorporated in their entirety.

SEQUENCE LISTING

The instant application contains a Sequence Listing which has been submitted in ASCII format via EFS-Web and is hereby incorporated by reference in its entirety. Said ASCII copy, created on Aug. 21, 2013, is named 18744-0055_SL.txt and is 12,486 bytes in size.

The present invention relates to monomeric and multimeric peptidic compounds which have antimicrobial activity, particularly against Gram-positive and Gram-negative bacteria. Further, the present invention refers to compositions comprising said peptidic compounds for medical use, for use as a disinfectant and/or detergent or for use as a preservative.

The increased occurrence of multidrug resistant microorganisms has prompted renewed interest in the development of novel antimicrobial agents. The drive to produce newer agents targeting novel sites that may circumvent resistance is critical for the long-term control of bacterial infection (Ref. 1).

The pharmaceutical industry has previously met this need by modifying existing antibiotics and developing newer antibiotics in a timely fashion. These successful efforts have produced the wide variety of currently available drug classes of antibiotics: beta lactams (penicillins, carbapenems, cephalosporins), glycopeptides, macrolides, ketolides, aminoglycosides, fluoroquinolones, oxazolidinones, and others (Ref. 2). Recently, however, microorganisms which are resistant against most or all of the known classes of antibiotics have been detected. Thus, there is an increased need for novel antibiotic compounds.

Antimicrobial peptides are components of the nonspecific immune system that represent a promising class of anti-infective agents. Although their mode of action is not well understood, they are believed to have multiple targets, including the cytoplasmic membrane and the processes of cell division and macromolecule synthesis (Ref. 3).

A review of peptide antibiotics has been published by R.E.W. Hancock (Ref. 4). The review focuses primarily on the advantages and disadvantages of cationic antimicrobial peptides (AMPs) when compared with conventional antibiotics, and summarizes recent clinical developments with these peptides. They can be defined as being short (10-50 amino acids), with an overall positive charge (generally +2 to +9) and a substantial proportion (≥30% or more) of hydrophobic residues. These properties permit the peptide to fold into an amphiphilic structure in three dimensions, often upon contact with membranes, so they form separate patches rich in positively charged and hydrophobic amino acids.

AMPs exhibit a broad spectrum of killing activity in vitro against various targets, such as bacteria, fungi, enveloped viruses, parasites and even tumour cells (Ref. 5 and 6).

Within the last 15 years, almost 900 AMPs have been identified across species and are now recognized as essential components of the innate immune system (Ref. 7). Magainins, e.g. magainin 2 and PGLa, are among the best studied AMPs. They are linear peptides that were originally isolated from the skin of the African frog *Xenopus laevis*. Magainins are α-helical ionophores that possess two important activities: a broad antimicrobial spectrum and an anti-endotoxin activity (Ref. 8).

A large family of AMPs in mammals is represented by cathelicidins. They are AMPs bearing an amino-terminal cathepsin L inhibitor domain (cathelin). The C-terminal 37 amino acid domain of the only human cathelicidin h-CAP 18, LL-37, is an amphipathic, helical peptide that exerts broad antimicrobial activity (Ref. 9).

Various synthetic peptides have been assayed in vitro and in vivo. For example, U.S. Patent Application No. 60/651,270 discloses antimicrobial hexapeptides and lipoderivatives thereof active against a range of pathogens. These peptides are particularly effective in the treatment of fungal and bacterial diseases in animals and demonstrate the potential to promote the bactericidal activity of conventional antibiotics, such as polymyxin B, against multidrug resistant bacteria.

WO 2006/006195 discloses antibacterial peptides, i.a. a peptide having the sequence QKKIRVRLSA (SEQ ID NO: 1). Although these peptides show antimicrobial activity, they are too unstable for practical use. Indeed, the N-terminal Gln provides pyroglutamic derivatives, the content of which increases during the product storage.

The present invention provides methods for using and making novel antimicrobial peptidic compounds to treat and/or prevent infectious diseases.

These novel peptidic compounds were identified by a sequence scanning process and an elongation step on a linear decapeptide. The peptide synthesis, carried out in solid phase by Fmoc/tBu chemistry, allowed to isolate libraries of peptides having an increased antibacterial activity when compared to the original sequence SEQ ID NO 1 as disclosed in WO 2006/006195.

A subject-matter of the present invention is a peptidic compound having a length of up to 35 amino acid residues comprising an amino acid sequence represented by the general formula (Ia):

$$Z\text{-}[K]_n\text{-}K\text{-}I\text{-}R\text{-}V\text{-}R \qquad (\text{SEQ ID NO: 25})$$

wherein K is an amino acid residue with a lysine side chain, particularly L- or D-lysine, or another amino acid residue with a positively charged side chain, I is an amino acid residue with an isoleucine side chain, particularly L- or D-isoleucine, R is an amino acid residue with an arginine side chain or an N-alkyl substituted guanidine side chain, particularly L- or D-arginine, V is an amino acid residue with a valine side chain, particularly L- or D-valine, wherein one of the amino acid residues K, I, R and V may be replaced by an amino acid residue with an alanine side chain, particularly L- or D-alanine, Z is the N-terminal group of the peptidic compound which comprises at least one amino acid residue and is selected from (i) an aromatic amino acid residue or a di-, tri- or tetrapeptidyl group comprising at least one aromatic amino acid residue, wherein the aromatic amino acid residue is particularly selected from tryptophans, N-methyltryptophane, phenylalanine, β-phenylalanine, naphthylalanine, β-naphthylalanine, β-diphenylalanine, β-(4,4'-biphenyl)alanine, β-anthracen-9-ylalanine and β-indol-3-ylalanine, or substituted derivatives thereof, (ii) an aliphatic amino acid residue or a di-, tri-, tetrapeptidyl group comprising at least one aliphatic amino acid residue, wherein the aliphatic residue is particularly selected from α-amino acid residues comprising an aliphatic, preferably a branched aliphatic side chain of at least 3 C-atoms,
(iii) a pyroglutamic acid (pyrE) residue or a di-, tri- or a tetrapeptidyl group comprising an N-terminal pyroglutamic acid residue,
(iv) a residue Q* or a di-, tri- or tetrapeptidyl group comprising an N-terminal Q*-residue,
   wherein Q* is a protected amino acid residue with a glutamine side chain, particularly a protected L-glutamine residue, and
(v) combinations of any one of (i)-(iv), e.g. (i) and (iii), (i) and (iv), (ii) or (iii) and (ii) or (iv),
   and n is 0 or 1.

In a preferred embodiment, the present invention relates to a peptidic compound having a length of up to 35 amino acid residues comprising an amino acid sequence represented by the general formula (Ib):

```
Z-[K]_n-K-I-R-V-R-L-S-A,    (SEQ ID NO: 26)
``` wherein K, I, R, V, Z and n are as defined above,
A is an amino acid residue with an alanine side chain, particularly L-alanine,
S is an amino acid residue with a serine side chain, particularly L-serine,
L is an amino residue with a leucine side chain, particularly L-leucine, and
wherein one of the amino acid residues K, I, R, L, V and S may be replaced by an amino acid residue with an alanine side chain.

In a further embodiment, the present invention refers to a multimeric compound comprising a plurality of peptidic compounds as defined above, wherein the individual peptidic compounds are covalently linked, e.g. by multifunctional, e.g. di- or trifunctional moieties, such as di- or trifunctional amino acids.

The present invention refers to peptidic compounds. The term "peptidic compounds" encompasses compounds, which at least partially comprise amino acid building blocks or analogues thereof, which are linked by covalent bonds, preferably carboxamide bonds. The building blocks are preferably selected from amino-carboxylic acids, e.g. α-amino carboxylic acids or other types of carboxylic acids, e.g. β- or even ω-amino carboxylic acids. The amino acid building blocks may be selected from genetically encoded L-α-amino carboxylic acids and/or their D-enantiomers and/or from non-naturally occurring amino acid building blocks. The individual building blocks of the peptidic compounds are linked by covalent bonds, e.g. carboxamide, carbamate, ester and thioester bonds. The peptidic compounds of the present invention may be linear or cyclic. Monomeric peptidic compounds have a length up to 35 amino acid residues, and preferably a length of at least 8, more preferably at least 10 and up to 15 amino acid building blocks.

In one embodiment, the peptidic compounds of the invention comprise an N-terminal group Z which comprises an aromatic amino acid residue, preferably an α-amino acid residue comprising at least one mono- or polycyclic aromatic ring, preferably at least one bi- or tricyclic aromatic ring, e.g. phenyl, naphthyl, anthracenyl, diphenyl, indolyl, etc., or a di-, tri- or tetra-peptidyi group comprising at least one aromatic amino acid building block as described above.

Specific examples for aromatic amino acid residues are tryptophane, N-methyltryptophane, phenylalanine, β-phenylalanine, naphthylalanine, β-naphthylalanine, β-diphenylalanine, β-(4-4'-biphenyl)alanine, β-anthracen-9-ylalanine and 3-indol-3-ylalanine, or substituted, e.g. mono- or polyalkyl substituted derivatives thereof. More preferably, the aromatic amino acid residue comprises a tryptophane side chain (W), e.g. L (or D)-tryptophane.

In a further embodiment, the peptidic compounds of the invention comprise an N-terminal group Z which comprises an aliphatic amino acid residue, preferably an α-amino acid residue comprising an aliphatic, more preferably a branched aliphatic side chain of at least three C-atoms, e.g. 3, 4, 5, 6 or 7 C-atoms or a di-, tri- or tetra-peptidyl group comprising at least one aliphatic amino acid building block as described above. Specific examples for aliphatic amino acid residues are branched alkyl, e.g. methyl derivatives of 2-amino pentanoic acid, 2-amino hexanoic acid or 2-amino heptanoic acid or the L- or D-enantiomeric forms thereof. More preferably, the aliphatic amino acid residue comprises a leucine side chain (L), e.g. L-leucine.

In a further embodiment of the invention, the peptidic compound comprises an N-terminal group which is a pyroglutamic acid (pyrE) residue or a di-, tri- or a tetra-peptidyl group comprising an N-terminal pyroglutamic acid residue.

In still a further embodiment of the present invention, the peptidic compound comprises an N-terminal group, which is a Q*-residue, wherein Q* is a protected amino acid residue with a glutamine side chain, particularly a protected L-glutamine, or a di-, tri-, or tetra-peptidyl group comprising an N-terminal Cr-residue for a derivative thereof. Preferred examples of Q*-residues are dipeptidyl residues X-Q, wherein X is an amino acid residue different from Q, such as G (glycine) or a Q-residue, wherein the N-terminal amino acid and/or the carboxyl side chain group is protected, e.g. by acyl, such as acetyl groups, amino groups etc.

In still a further embodiment, the peptidic compound of the present invention comprises a combination of an aromatic amino acid residue and an N-terminal pyroglutamic acid residue or a combination of an aromatic amino acid residue and an N-terminal Q* residue.

In an especially preferred embodiment, the N-terminal group Z of the peptidic compound is selected from Ar, Ar-Q, Q* such as G-Q or Acetyl-Q, Q*-Ar such as G-Q-Ar or Acetyl-Q-Ar, pyrE and pyrE-Ar, wherein Ar is an aromatic amino acid residue as defined above.

Specific examples of peptidic compounds according to the present invention comprise an amino acid sequence selected from:

| WKKIRVRLSA | (SEQ ID NO: 6) |
| pyrEWKIRVRLSA | (SEQ ID NO: 27) |
| GQWKIRVRLSA | (SEQ ID NO: 14) |
| Acetyl-QWKIRVRLSA. | (SEQ ID NO: 12) |
| Aoa-QWKIRVRLSA | (SEQ ID NO: 16) |
| (GQWKIRVRLSA)₂ K-β-Ala | (SEQ ID NO: 19) | wherein pryE is a pyroglutamic acid residue, Aoa is an 8-amino octanoic acid residue, β-Ala is a β-alanine residue and wherein the above peptides are optionally amidated at their C-termini.

In a preferred embodiment, the invention refers to a multimeric compound comprising a plurality of peptidic compounds as described above. For example, a multimeric compound of the present invention may comprise 2, 3, 4, 5, 6, 7, 8 or more of the peptidic compounds. The multimeric compound may comprise the peptidic compounds multimerized on a matrix, e.g. a matrix based on a polypeptide, a mono-, oligo- or polysaccharide or an organic polymer, preferably a linear organic polymer. For example, the matrix may be selected from poly (N-alkyl(meth)acrylamide), poly (N,N-dialkyl(meth)acrylamide), polymelamine, dextrane, cyclodextrine, polyethyleneglycol and/or polyvinylpyrrolidone. The coupling of the peptidic compounds to the matrix preferably occurs via the N- and/or C-termini of the peptidic compound, e.g. using homo- and/or hetero-bifunctional linkers which allow coupling to reactive groups, e.g. hydroxy-, amino-, thiol- or carboxyl groups on the matrix.

In a further preferred embodiment, the multimeric compound has a branched, particularly a dendrimeric structure.

In a still further embodiment, the multimeric compound is selected from:

  (IIa)

wherein R is a peptidic compound as defined in any one of claims 1-6, $Y^1$ is a covalent bond or a bifunctional linker, e.g. a dialcohol such as propylene glycol, a dicarboxylic acid such as succinic acid, a diamine such as ethylene diamine, an amino acid, a hydroxy carboxylic acid, e.g. a hydroxy alcanoic acid, or a diisocyanate, and m is 0 or a positive whole number, and m' is 0 or 1,

  (IIb)

wherein R is a peptidic compound as defined in any one of claims 1-6, $Y^{1'}$ is in each case independently a linker having a functionality of at least 3, e.g. a trifunctional amino acid such as lysine, ornithine, norlysine, aminoalanine, aspartic acid or glutamic acid, and $Y^2$ is a linker having a functionality of at least 2, and $n_1$ and $n_2$ in each case independently are a whole number of at least 2, preferably 2, 3 or 4, more preferably 2,

  (IIc)

wherein R is a a peptidic compound as defined in any one of claims 1-6, $Y^{1'}$ and $Y^{2'}$ are in each case independent linkers having a functionality of at least 3, e.g. a trifunctional amino acid such as lysine, ornithine, norlysine, aminoalanine, aspartic acid or glutamic acid, $Y^3$ is a linker having a functionality of at least 2 and $n_1$, $n_2$ and $n_3$ are in each case independently whole numbers of at least 2, preferably 2, 3 or 4, more preferably 2.

The multimeric compound (IIa) is a multimeric linear compound, wherein a plurality of peptidic compounds are connected via covalent bonds and/or homo- or hetero-bifunctional linkers $Y^1$. Preferably, the multimeric compound comprises up to 8, more preferably up to 4 units of peptidic compounds (Ia) or (Ib).

The multimeric compounds (IIb) and (IIc) are branched compounds, wherein individual peptidic units R are connected via linkers having a functionality of at least 3. In a preferred embodiment, the multimeric compound (IIb) comprises 4 peptidic units and has the structure:

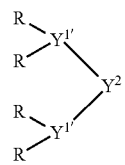

In a further preferred embodiment, the multimeric compound (IIc) comprises 8 peptidic units and has the structure:

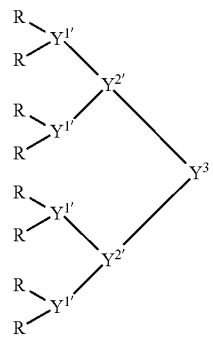

In a still further embodiment of the present invention, the peptidic and multimeric compounds comprise at least one modification, particularly selected from a lipid, amide, ester, acyl and/or alkyl moiety attached thereto, e.g. attached to an N-terminal group, a C-terminal group and/or a side chain group. Preferred are N- and/or C-terminal modifications.

An especially preferred modification is the attachment of at least one lipid moiety, which is at least one amino carboxylic acid comprising a linear or cyclic, saturated or mono- or polyunsaturated hydrocarbon group having 3 to 25 and preferably 5 to 25 C-atoms, e.g. 5-amino valeroic acid, 8-amino octanoic acid or 2-amino decanoic acid. Preferably, the lipid moiety is attached to the N- and/or C-terminus of the compound. Lipid moieties may e.g. be attached to free N-termini or C-termini of peptidic compounds and/or multimeric compounds. Lipid moieties, however, may also be attached to N- and/or C-terminal linkers, e.g. as described for compounds (IIa), (IIb) and (IIc). In a preferred embodiment of compounds (IIb) and (IIc), the C-terminal linkers $Y^2$ and $Y^3$ are trifunctional linkers to which a lipid moiety may be attached.

A further preferred embodiment is the attachment of acyl, e.g. acetyl groups to the N-termini and/or the amidation of free C-termini.

The compounds of the present invention may have antimicrobial activity, particularly activity against pathogenic organisms selected from prokaryotic organisms, e.g. eubacteria or archaea, and eukaryotic organisms, e.g. fungi, algae or parasites. Preferably, the compounds have antibacterial activity, e.g. activity against Gram-negative and/or Gram-positive bacteria.

The compounds of the present invention may also have anti biofilm activity. Infections related to the insertion of medical devices in the body are rising with time. The process involves the adhesion of organism onto devices, the multiplication and the biofilm formation. Biofilms are difficult to eradicate with conventional antimicrobial agents, being the antimicrobial resistance determined by some peculiarity of biofilm growth (Ref. 10). Consequently, in a further aspect, the compounds according to the invention can also be used to prevent or inhibit the growth and proliferation of biofilm embedded bacteria such as, but not limited to: *Escherichia coli, Klebsiella pneumoniae, Acinetobacter baumannii, Pseudomonas aeruginosa, Staphylococcus epidermidis,* and *Staphylococcus aureus.*

A further subject-matter of the present invention is a composition for medical use comprising at least one compound as defined above, e.g. a peptidic or multimeric compound as defined above, together with pharmaceutically acceptable carriers, diluents and/or adjuvants. For use in human or veterinary medicine, the composition is preferably in form of a pharmaceutical dosage form selected from solids, liquids or gels and combinations thereof, e.g. as an eyewash, mouthwash, ointment, aerosol or topical product. The pharmaceutical dosage form comprises a pharmaceutically effective amount of the monomeric or multimeric peptidic compound of the invention, i.e. an amount of the active agent which is effective for the treatment and/or prevention of disorders caused by, associated with or accompanied by the presence of pathogenic organisms. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

The actual amount of the active agent in the pharmeutial dosage form of the invention may vary depending on the administration route and the type and severity of disorder to be treated. To achieve the desired effect(s), the peptidic monomeric or multimeric compound may be administered as single or divided dosages, for example, of at least about 0.01 mg/kg to about 200 to 550 mg/kg, of at least about 0.01 mg/kg to about 100 to 300 mg/kg, at least about 0.1 mg/kg to about 50 to 100 mg/kg or at least about 1 mg/kg to about 10 to 50 mg/kg of body weight or at least about 1 mg/kg to about 20 mg/kg of body weight, although other dosages may provide beneficial results.

To prepare the pharmaceutical composition, the peptides of the invention are synthesised or otherwise obtained, purified as necessary or desired, and then preferably lyophilised and stabilized. The peptide can then be adjusted to the suitable concentration and optionally combined with the other pharmaceutically acceptable agents.

Thus, one or more suitable unit dosage forms comprising the therapeutic peptides of the invention can be administered by a variety of routes including oral, topical, parenteral (including subcutaneous, intravenous, intramuscular and intraperitoneal), vaginal, rectal, dermal, transdermal, intrathoracic, intrapulmonary and intranasal (respiratory) routes.

For topical administration, the active agents may be formulated as is known in the art for direct application to a target area, for example nails and skin. Forms chiefly conditioned for topical application take the form, for example, of laquers, creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include wound dressings, coated bandages or other polymer coverings, ointments, creams, lotions.

In a further preferred embodiment, the monomeric or multimeric compounds or the composition of the present invention are used in veterinary medicine applications. Hence, the present invention also refers to a veterinary composition comprising at least one compound as described above.

Still a further embodiment of the present invention refers to a composition for use as a disinfectant and/or detergent comprising at least one compound as described above or for use of a preservative, e.g. a preservative for medical, cosmetic or food products, comprising at least one compound described above.

A further embodiment of the present invention refers to a composition for decreasing growth or proliferation of biofilm embedded microorganisms comprising at least one compound as described above.

In a still further embodiment of the present invention, the peptidic compounds and compositions are used to treat the surface of a device, preferably a medical device which is desirable to be microorganism-resistant. In particular, according to this aspect of the invention the peptidic compounds and their composition are coated on the surface of a medical device, in particular by binding, coating and/or embedding the compounds and compositions of the invention on a medical device. Examples of medical devices include tubing and cannulae, stents, surgical instruments, catheters, pacemakers, prosthetic heart valves, prosthetic joints, voice prostheses, contact lenses, and intrauterine devices.

Further, the present invention shall be explained in more detail by the following figures and examples.

BRIEF DESCRIPTION OF THE DRAWINGS

In particular, FIG. 2a shows the exposure of the *P. aeruginosa* ATCC 27853 24-hours biofilm to different concentrations of the ID24 compound of the invention. Number of replicates/concentration is n=2.

FIG. 2b on the other side shows the exposure of *P. aeruginosa* ATCC 27853 24-hours biofilm to different concentration of the colistin sodium methanesulfonate (CMS). Number of replicates/concentration is n=2.

EXAMPLES

Materials

Figure 1:
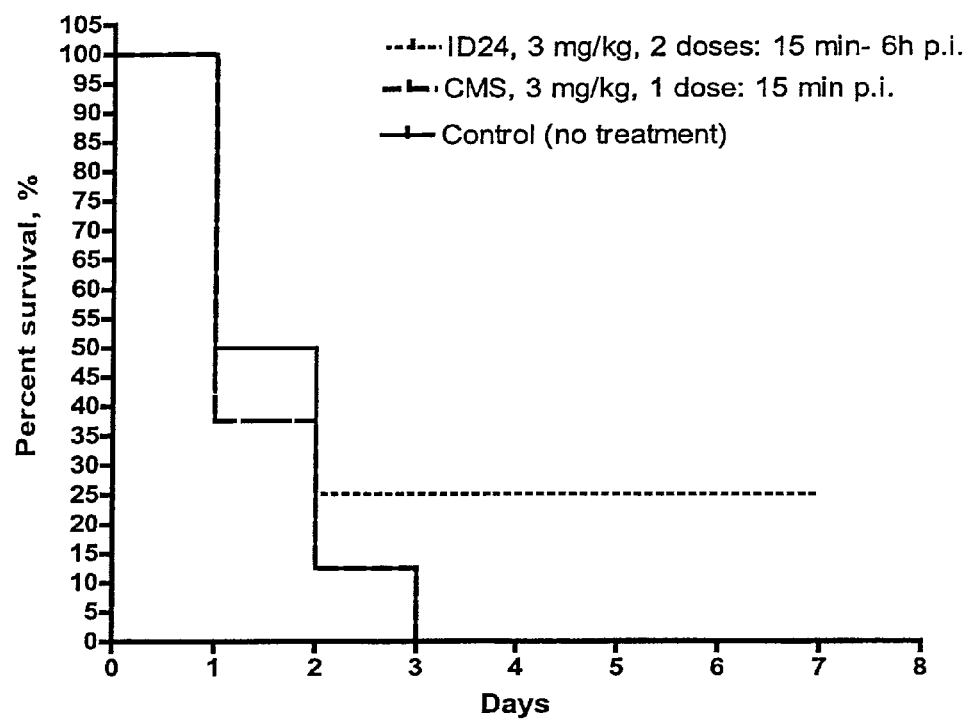
FIG. 1 shows a Kaplan-Meyer survival plot of the efficiency in vivo tests, where the dimeric peptidic compound ID24 (SEQ ID NO:24, cf. Table 4) of the invention is compared with the reference antibiotic compound colistin sodium methanesulfonate (CMS) at the same regimen dose in a septicemia model in mice.

Solvents, all of HPLC grade, were obtained from Sigma Aldrich (St. Louis, Mo., US) and used without further purification. N,N-diisopropylethylamine (DIPEA), piperidine, trifluoroacetic acid and triisopropylsilane were purchased from Aldrich and Fluka (St. Louis, Mo., US). Fmoc-aminoacids, HOBT, HBTU and resins were supplied from ChemImpex International (Wooddale, Ill.) and Merck (Darmstadt, Germany).

Peptide Synthesis. All the peptides were synthesised by solid phase synthesis on a MultiSynTech Syro (Witten, Germany), using Fmoc/tBu chemistry. Coupling activation was carried out by HOBt/DIPEA/HBTU (1/2/0.9) in DMF and the Fmoc-protection on amine was removed employing 40% piperidine in NMP. Side chain protecting groups were: tert-butyl ester for Glu and Asp; trityl for His, Gln and Asn; 2,2,4,6,7-pentamethyldihydro-benzofuran-5-sulfonyl (Pbf) for Arg; tent-butyl ether for Ser, Thr and Tyr; tert-butyloxycarbonyl (Boc) for Lys, Pro and Trp. Fmoc-Lys(Fmoc)-OH was the amino acid used to synthesize dimeric and tetrameric peptides. Fmoc-5-amino valeric acid (5-Ava) and Fmoc-8-amino octanoic acid (8-Aoa) were used to carry out lipidation at N- and/or C-terminus both on linear and dimeric peptides. Tetrameric, dimeric and linear peptides were prepared on Rink amide 4-benzhydrylamine resin (MBNA), evaluating by spectrophotometric measurements the final loading in free amino groups, while acid peptides were prepared on a 2-chlorotrityl chloride resin. All peptides were cleaved from the resins and deprotected by treatment with trifluoroacetic acid, water and triisopropylsilane (TIPS, 95:2.5:2.5). The crude peptides, obtained by precipitation in diethyl ether, were purified by Waters HPLC-UV (Milford, Mass.) on a $C_{12}$ Phenomenex column and characterized by Bruker MALDI-TOF spectrometry (Billerica, Mass.).

Determination of MIC. MICs were determined in MHB by the broth microdilution methodology, according to CLSI procedure (formerly NCCLS, Ref. 11) by using final bacterial inocula of $1-5\times10^5$ CFU/mL. Assays were performed in sterile 96-well microtiter plates with round bottom wells (Corning Costar). Plates were incubated at 37° C. and read after 20-24 h. MIC was defined as the lowest drug concentration causing complete suppression of visible bacterial growth. All compounds were dissolved in (5% v/v DMSO).

Example I

2-$X_1$ minilibrary synthesis

The peptide synthesis was performed on a 2-chlorotrityl chloride resin, as described above. Six linear acid peptides, having the general sequence H-$X_1$-KKIRVRLSA-OH with $X_1$=F, I, L, V, W, Y (SEQ ID NO: 28), were synthesized and combined in equimolar amounts. The resulting crude peptide mixture was purified on $C_{12}$ HPLC column, in order to remove salts and scavengers coming from cleavage, and analysed by LC-MS (ESI/Ion Trap) coupled with a HPLC system (Agilent Technologies, Santa Clara, CA), eluting components with a gradient mode (B 5→95% in 20 min; A 0,1% TFA in water, B 0.1% TFA in acetonitrile) at a flow rate of 1,0 ml/min. MS (LC-MS ESI/Ion Trap): (ID2) calcd for $C_{56}H_{100}N_{18}O_{12}$ ($X_1$=F) is (M) 1216, found is 1217 (M+H); (ID3) calcd for $C_{53}H_{102}N_{18}O_{12}$ ($X_1$=I) is (M) 1182, found is 1183 (M+H); (ID4) calcd for $C_{53}H_{102}N_{18}O_{12}$ ($X_1$=L) is (M) 1182, found is 1183 (M+H); (ID5) calcd for $C_{52}H_{100}N_{18}O_{12}$ ($X_1$=V) is (M) 1168, found is 1169 (M+H); (ID6) calcd for $C_{58}H_{101}N_{19}O_{12}$ ($X_1$=W) is (M) 1255, found is 1256 (M+H); (ID7) calcd for $C_{56}H_{100}N_{18}O_{13}$ ($X_1$=Y) is (M) 1232, found is 1233 (M+H).

Example II

3-$X_1$ minilibrary synthesis

The peptide synthesis was performed as described above. Six linear acid peptides, having the general sequence H-Q-$X_1$-KIRVRLSA-OH with $X_1$=F, I, L, V, W, Y (SEQ ID NO: 29), were synthesized and combined in equimolar amounts. The crude peptide mixture was purified as reported in the Example I. MS (LC-MS ESI/Ion Trap): (ID8) calcd for $C_{55}H_{96}N_{18}O_{13}$ ($X_1$=F) is (M) 1216, found is 1217 (M+H); (ID9) calcd for $C_{53}H_{101}N_{18}O_{13}$ ($X_1$=I) is (M) 1197, found is 1198 (M+H); (ID10) calcd for $C_{52}H_{98}N_{18}O_{13}$ ($X_1$=L) is (M) 1182, found is 1183 (M+H); (ID11) calcd for $C_{51}H_{96}N_{18}O_{13}$ ($X_1$=V) is (M) 1168, found is 1169 (M+H); (ID12) calcd for $C_{57}H_{97}N_{19}O_{13}$ ($X_1$=W) is (M) 1255, found is 1256 (M+H); (ID13) calcd for $C_{55}H_{96}N_{18}O_{14}$ ($X_1$=Y) is (M) 1232, found is 1233 (M+H).

Example III

Linear acid peptide synthesis: ID1, ID6 and ID14

The acid peptide synthesis was performed as described above. After synthesis, the crude peptides were purified by HPLC-UV by a gradient B 5→95% in 20 min and characterized by MALDI-TOF. The mass values (M+H) were: (ID1) calcd is (M) 1197, found is 1198 (M+H); (ID6) calcd is (M) 1255, found is 1256 (M+H); (ID14) calcd is (M) 1383, found is 1384 (M+H).

Example IV

N-acylated linear amido peptide synthesis: ID15, ID16 and ID17

The amido peptide synthesis was performed on a Rink amide resin, as described above in Peptide Synthesis paragraph. After synthesis, the crude peptides were purified by HPLC-UV and characterized by MALDI-TOF, as reported in the Example I. The mass values (M+H) were: (ID15) calcd is (M) 1395, found is 1397 (M+H); (ID16) calcd is (M) 1395, found is 1397 (M+H); (ID17) calcd is (M) 1337), found is 1339 (M+H).

Example V

Dimeric peptide synthesis: ID18, ID19 and ID20

The peptide synthesis was performed as described above. After synthesis, the crude peptides were purified by HPLC-UV and characterized by MALDI-TOF as reported in the Example I. The mass values (M+H) were: (ID18) calcd is (M) 2694, found is 2696 (M+H); (ID19) calcd is (M) 2807, found is 2808 (M+H); (ID20) calcd is (M) 2691, found is 2692 (M+H).

Example VI

Dimeric lipidated peptide synthesis: ID21, ID22, ID23 and ID24

The peptide synthesis was performed as described above. After synthesis, the crude peptides were purified by HPLC-UV and characterized by MALDI-TOF as reported in the Example I. The mass values (M+H) were: (ID21) calcd is (M) 2891, found is 2892 (M+H); (ID22) calcd is (M) 2891, found is 2893 (M+H); (ID23) calcd is (M) 2859, found is 2862 (M+H); (ID24) calcd is (M) 2763, found is 2764 (M+H).

Example VII

In Vitro Citotoxicity Assay

HeLa (Human epithelial carcinoma cell line), HepG2 (Human hepatocellular liver carcinoma cell line) and HaCat (human keratinocyte) were grown to confluence and then plated at 20,000, 12,500 and 30,000 cells per well (the optimal cell count for each cell line has been previously determined). After 24 hours, ID24 in DMEM without FBS was added at concentration ranging from 800 and 100 ug/ml. As positive controls 100 uL of cells washed with medium without serum that represent 100% viability and, as negative, 100 uL medium without serum were also added.

After 24 hours of incubation at 37° C. in a 5% v/v $CO_2$ atmosphere, 10 ul MTT Reagent [3-(4,5-dimethylthiazol-2-yl)-2,5-diphenyl tetrasodium bromide, final concentration 0.5 mg/mL) was added to each well and incubated for 2 to 4 hours. Solubilization of formazan, formed by metabolic reduction of MTT, was obtained using the stop mix solution (10% w/v sodium dodecyl sulphate, 45% v/v dimethyl formamide, adjusted to pH 4.5 with glacial acetic acid). The plates were read in a microplate spectrophotometer. (Biorad, Benchmark plus). Cultures exposed to ID24 or exposed to the medium alone were measured spectrophotometrically at dual wave-length (565-650 nm). The experiment was carried out in three replicates.

Example VIII

In Vitro Haemolysis

The haemolysis was determined by two different assays. One of them was adapted from the method of Shin et al. (Ref. 12), by using only fresh human erythrocytes. In the second one, a ID24 solution was incubated in whole blood.

First Method

The haemolysis assay was adapted from the method of Shin et al. (Ref. 12). Fresh human erythrocytes were used to test the haemolytic activities of the peptides. Whole blood was collected in a sterile tube with a 4% w/v sodium citrate solution (in a 1:10 ratio sodium citrate:whole blood), put in ice and centrifuged at 1000 g for 5 minutes at 4° C.

The supernatant, including the leucocytes above the erythrocyte pellet, was removed carefully and discarded. Intact erythrocytes were washed three times with 2 volumes (1 mL) of prechilled pyrogen-free saline (PBS 1×). Erythrocyte suspensions were adjusted to 0.8% (8 ul in 1 mL or 160 uL in 20 mL) of PBS 1×.

Serial two-fold dilutions of ID24 were prepared in PBS 1× for the haemolysis assay and 100 uL aliquots were added to equal volumes of 0.8% of erythrocyte suspension in PBS 1× in sterile 96-well microtiter plates (Nunc) in triplicate. The plates were incubated at 37° C. for 2 h.

Subsequently, intact erythrocyte were pelletted by centrifugation at 1000 g for 5 minutes at 4° C. One hundred microliters of supernatant from each well was transferred accordingly to a new 96-well microtiter plate, and the amount of haemoglobin released into the supernatant was determined by reading the absorbance at 414 nm against a reference wavelength of 490 nm. A positive control with 100 uL of 0.4% erythrocyte lysed in 1% Triton X 100 in PBS 1× (200 uL of erythrocytes suspension 0.8% in PBS 1× and 200 uL of PBS 1× with 2% (4 uL) Triton X 100) was taken as 100% lysis. The negative control was eryth Second Method Whole blood was collected in a sterile tube with with a 4% w/v sodium citrate solution (in a 1:10 ratio sodium citrate: whole blood) and conserved in ice. Serial dilutions of ID24 (1 mg/mL to 62.5 ug/mL) were added to whole blood in a ratio 1:1 or 1:10. The haemolytic potential was expressed relative to saponine, added in the same ratio, considered as 100% haemolysis. The negative control was whole blood in physiologic solution, which gave minimal lysis. 100 uL aliquots of each suspension were added in sterile 96-well microtiter plates (Nunc) in triplicate. The plates were incubated at 37° C. for 30 minutes.

Subsequently, the suspension were pelletted by centrifugation at 1000 g for 10 minutes at 4° C. One hundred microliters of supernatant from each well was transferred accordingly to a new 96-well microtiter plate, and the amount of haemoglobin released into the supernatant was determined by reading the absorbance at 560 nm.

Example IX

In Vivo Efficacy in a Septicaemia Model in Mice

ID24 was administered intravenously to mice infected intraperitoneally with $7.5×10^2$ CFU of *E. coli* EC47 in a final volume of 0.5 mL. In particular, ID24 was administered at doses of 3 mg/kg at 15 min and 6 h post-infection. Colistin sodium methanesulfonate (CMS) was administered as single injection 15 min post-infection at a dose of 3 mg/kg.

Animals

Female ICR mice (Harlan Italy, San Pietro al Natisone, Italy) weighing 25 gr on the day of experiment were used. Mice were housed for at least 5 days in a temperature and humidity controlled room before starting experiment and were fed with standard laboratory chow and water ad libitum.

Test and Reference Compounds

Test and reference compounds, ID24 and colistin sodium methanesufonate (CMS) respectively, were dissolved in 0.1 M phosphate-buffered saline pH 6.9, at the required drug concentrations. Solutions were made just before administration, and stored at 4° C. until the end of scheduled treatments, ID24 MIC value on *E. coli* EC47 strain is 2 ug/mL [MIC was determined by the broth microdilution method in Muller Hinton medium (NCCLS guidelines), using bacterial inoculum of approximately $10^5$ CFU/mL].

Preparation of Infecting Suspension

A frozen vial of *Escherichia coli* EC47 strain, was used to inoculate 50 mL Difco Brain Heart Infusion broth, the culture was incubated on a rotary shaker water bath (New Brunswick Scientific, N.J., USA) for 20 hours at 35° C. and then diluted 1:1,000,000 in 5% Difco bacteriological mucin. The actual inoculum size was determined by plating two 0.025 mL aliquots of 10-fold solutions of the suspension on Difco Todd Hewitt agar plates.

Animals were infected intraperitoneally with $7.5×10^2$ CFU of *Escherichia coli* EC47 in a final volume of 0.5 mL. This inoculum was sufficient to kill 100% of the untreated animals within 72 h of infection.

Antibiotic Treatment

ID24 was administered at doses of 3 mg/kg, at 15 min and 6 h post-infection. The overall dose is 6 mg/kg. Colistin sodium methanesulfonate (CMS) was administered at one dose, namely 3 mg/kg in a single injection at 15 min post-infection.

Treatment was by intravenous route (0.25 mL/mouse); eight animals were treated with each dose of each antibiotic. Mortality was recorded once daily for 7 days following the bacterial inoculation.

Example X

Experimental Procedure of Biofilm Eradication

An exponential phase inoculum of *Pseudomonas aeruginosa* ATCC 27853 of approximately $1×10^7$ CFU/mL was poured into a reagent reservoir of Innovotech plates for MBEC™ High-throughput assay (Innovotech Inc., Edmonton, Canada). 22 mL of inoculum were added to the trough and the peg lid was placed onto. The device was placed on the shaking incubator at 80 rpm in a humidified box at 37° C.

After 24 hours of incubation, the pegs were rinsed into a plate containing 200 uL of physiological solution to remove loosely adherent planktonic cells from the biofilm and then were put in a microplate containing 200 uL of different antibiotic solutions serially diluted in TSB.

Following 4 hours of contact and incubation at 37° C. on the shaking incubator, the peg lid was removed from the trough and submersed in a rinse plate for 2 minutes.

Then a new microtitre with saline solution containing the sample pegs was put in the tray of the ultrasonic cleaner and sonicated for 30 minutes to disrupt biofilm from the surface of the 96 pegs.

Duplicate 0.01 or 0.005 mL aliquots of ten fold serial dilution of each well, were spread on MHA plate and colonies were read for viable cell counting after 24 hours of incubation.

Example XI

In Vivo Acute Toxicity

Animals 9-10 weeks female CD1 mice (Charles River Lab. Italia s.r.l. Via Indipendenza, 11-23885 Calco (LC), Italy), weighing on average 28.23 g on the day of experiment were used. Mice were housed for 3 days in a temperature and humidity controlled room before starting experiment, and were fed with standard laboratory chow and water ad libitum.

Test Compound

ID24 was dissolved and sonicated in 0.9% w/v NaCl sterile solution (Sigma-Aldrich) for human administration at the dose concentrations 20 and 40 mg/kg. Compound preparation was conducted just before administration.

Administration of Antibiotic

Two doses of ID24 were administered with a single intraperitoneal injection to mice: 20 mg/kg and 40 mg/kg. Five animals were treated with each dose of antibiotic. Adverse symptoms were monitored daily for 7 days after injection.

Evaluation of Results

Survivals and clinical/behavioural signs were recorded daily for 14 days.

Observed Parameters

Main behavioural parameters and clinical signs provided by Irwin Test (Ref. 13).

The observation of all groups after a single dose injection, allow us to highlight the following symptoms and behavioural alterations:

20 mg/kg: no behavioural alterations;

40 mg/kg: no behavioural alterations.

No adverse symptoms, no behavioural alterations and no deaths were recorded after IP administration of ID24, also at the highest dose of 40 mg/kg.

Results

Minilibrary Construction and Determination of MICS

The linear decapeptide SEQ ID NO 1 described in WO 2006/006195 was optimized in terms of activity against gram-negative bacteria. This peptide was active when present as a tetrameric structure on a lysine core. In monomeric form, the peptide had only negligible activity. The optimization approach consisted of the synthesis of nine peptide minilibraries, obtained by a sequence scanning as reported schematically in Table 1.

TABLE 1

The nine decapeptide positional scanning libraries

| Scanning Entry* | Sequence (N-terminus $A_1$-C-terminus $A_{10}$) |
|---|---|
| 1-$X_n$ | O -$A_1$-$A_2$-$A_3$-$A_4$-$A_5$-$A_6$-$A_7$-$A_8$-$A_9$-$A_{10}$ |
| 2-$X_n$ | O -$A_2$-$A_3$-$A_4$-$A_5$-$A_6$-$A_7$-$A_8$-$A_9$-$A_{10}$ |
| 3-$X_n$ | $A_1$-O -$A_3$-$A_4$-$A_5$-$A_6$-$A_7$-$A_8$-$A_9$-$A_{10}$ |
| 4-$X_n$ | $A_1$-$A_2$-O -$A_4$-$A_5$-$A_6$-$A_7$-$A_8$-$A_9$-$A_{10}$ |
| 5-$X_n$ | $A_1$-$A_2$-$A_3$-O -$A_5$-$A_6$-$A_7$-$A_8$-$A_9$-$A_{10}$ |
| 6-$X_n$ | $A_1$-$A_2$-$A_3$-$A_4$-O -$A_6$-$A_7$-$A_8$-$A_9$-$A_{10}$ |
| 7-$X_n$ | $A_1$-$A_2$-$A_3$-$A_4$-$A_5$-O -$A_7$-$A_8$-$A_9$-$A_{10}$ |
| 8-$X_n$ | $A_1$-$A_2$-$A_3$-$A_4$-$A_5$-$A_6$-O -$A_8$-$A_9$-$A_{10}$ |
| 9-$X_n$ | $A_1$-$A_2$-$A_3$-$A_4$-$A_5$-$A_6$-$A_7$-O -$A_9$-$A_{10}$ |

*$X_n$ corresponds to a group of six aminoacids, containing: If n = 1, O = F, I, L, V, W, Y; if n = 2 O = K R, H, N, P, Q; if n = 3 O = G, A, S, T, D, E.

All natural aminoacids have been divided into three groups based on their chemical-physical properties. A total amount of 27 minilibraries, each one containing six peptide in equimolar amounts, were obtained and assayed against *E. coli* ATCC 25922 as reference strain. Activity values expressed in terms of MIC are listed in Table 2. MIC (Minimum Inhibitory Concentration) is defined as the lowest concentration inhibiting 100% of visible growth.

TABLE 2

The nine decapeptide positional scanning minlibraries: activity or resulting 27 peptide minilibraries against *E. coli* ATCC 25922

| Scanning Entry | MIC (ug/mL) E. coli | Scanning Entry | MIC (ug/mL) E. coli | Scanning Entry | MIC (ug/mL) E. coli |
|---|---|---|---|---|---|
| 1-$X_1$ | 125 | 4-$X_1$ | 250 | 7-$X_1$ | 125 |
| 1-$X_2$ | 125 | 4-$X_2$ | 250 | 7-$X_2$ | >250 |
| 1-$X_3$ | 125 | 4-$X_3$ | >250 | 7-$X_3$ | >250 |
| 2-$X_1$ | 62.5 | 5-$X_1$ | 125 | 8-$X_1$ | 62.5-125 |
| 2-$X_2$ | 62.5 | 5-$X_2$ | >250 | 8-$X_2$ | 250 |
| 2-$X_3$ | 125 | 5-$X_3$ | >250 | 8-$X_3$ | 250 |
| 3-$X_1$ | 31.25-62.5 | 6-$X_1$ | 125 | 9-$X_1$ | 125 |
| 3-$X_2$ | 250 | 6-$X_2$ | 250 | 9-$X_2$ | >250 |
| 3-$X_3$ | 125-250 | 6-$X_3$ | >250 | 9-$X_3$ | >250 |
| | | SEQ ID1[a] | >250 | | |

[a]inactive original 10-mer sequence

Four minilibraries, having a MIC of 62.5 ug/mL, were identified as more active than SEQ ID NO 1. These peptides were synthesized individually, in order to assay the activity of each sequence. The most active minilibraries—2-$X_1$, 2-$X_2$, 3-$X_1$ and 8-$X_1$—were opened and and the contribution of each residue at each sequence position to antimicrobial activity was evaluated. Moreover, modifications such as N- and C-acylation and dimerization on Lys-β-Ala or Lys-8-Aoa (8-amino octanoic acid) have been also performed on the more active sequences isolated from the minilibraries. In Table 3, the peptides belonging to minilibraries 2-$X_1$ e 3-$X_1$ tested against the Gram-negative strains *E. coli* ATCC 25922, *Pseudomonas aeruginosa* ATCC 27853 and *Klebsiella pneumoniae* ATCC 10031 and against the Gram-positive strain *Staphylococcus aureus* ATCC 25923 are listed. The other two most active minilibraries named 2-$X_2$ and 8-$X_1$ were also opened, but each peptide individually tested resulted to have an activity >128 ug/mL (data not shown).

TABLE 3

Minilibraries peptides were individually synthesised: MICs (ug/mL) against Gram-negative and Gram-positive bacteria are reported

| Minilibrary name | Name | Peptide sequence | MIC (ug/mL) | | | |
|---|---|---|---|---|---|---|
| | | | E. coli | P. aeruginosa | K. pneumoniae | S. aureus |
| 2-X$_1$ | ID2 | H-F-KKIRVRLSA-OH | 256 | 256 | 512 | 512 |
| | ID3 | H-I-KKIRVRLSA-OH | 256 | 256 | 512 | 512 |
| | ID4 | H-L-KKIRVRLSA-OH | 256 | 256 | 512 | >512 |
| | ID5 | H-V-KKIRVRLSA-OH | 512 | 512 | >512 | 512 |
| | ID6 | H-W-KKIRVRLSA-OH | 64-128 | 128 | 256 | 512 |
| | ID7 | H-Y-KKIRVRLSA-OH | 256 | 256 | >512 | >512 |
| 3-X$_1$ | ID8 | H-Q-F-KIRVRLSA-OH | 128 | 128 | >512 | >512 |
| | ID9 | H-Q-I-KIRVRLSA-OH | 512 | >512 | 512 | >512 |
| | ID10 | H-Q-L-KIRVRLSA-OH | 128 | 128 | >512 | >512 |
| | ID11 | H-Q-V-KIRVRLSA-OH | 256 | 256 | >512 | >512 |
| | ID12 | H-Q-W-KIRVRLSA-OH | 64 | 64 | >512 | >512 |
| | ID13 | H-Q-Y-KIRVRLSA-OH | >256 | >512 | >512 | >512 |
| | ID 1 | H-QKKIRVRLSA-OH | >512 | >512 | >512 | — |

The introduction of pyroglutamic acid or the dipeptide Gly-Gln can performed in position A$_1$ without affecting the activity of the peptide (data not shown). These modifications prevent pyroglutamate formation from cyclization of N-terminal glutamine.

Two selected peptides (SEQ ID NO 6 and 14) isolated from the two minilibraries named 2-X$_1$-W and 3-X$_1$-W, were synthesized in dimeric form (SEQ ID NO 18 and 19), in order to demonstrate the increased activity related to polyvalency in respect of their linear counterparts. The peptide SEQ ID NO 14 is a derivative of the selected peptide SEQ NO ID12 with a Gly introduced at the N-terminus in order to avoid cyclization of Gln. Furthermore, modifications such as lipidation with 5-aminovaleric acid (5-Ave) and 8-aminooctanoic acid (8-Aoa) at the N-terminus (SEQ ID NO 16, 16, 17, 21, 22 and 23) and at the C-terminus (SEQ ID NO 24) both of linear and dimeric peptides were performed and the resulting products tested.

In Table 4, MIC values of linear and dimeric peptides and their lipo-derivatives are reported.

TABLE 4

MIC values of linear and dimeric peptides and their lipo-derivatives.

| SEQUENCE NAME | Peptide sequence | MIC (ug/mL) | | | |
|---|---|---|---|---|---|
| | | E. coli | P. aeruginosa | K. pneumoniae | S. aureus |
| ID6 | H-W-KKIRVRLSA-OH (SEQ ID NO: 6) | 64-128 | 128 | 256 | 512 |
| ID14 | H-G-Q-W-KIRVRLSA-OH (SEQ ID NO: 6) | 64 | 64 | >512 | >512 |
| ID1 | H-QKKIRVRLSA-OH (SEQ ID NO: 1) | >512 | >512 | >512 | — |
| ID15 | H-8-Aoa-W-KKIRVRLSA-NH$_2$ (SEQ ID NO: 15) | 32 | >64 | >64 | ND |
| ID16 | H-8-Aoa-Q-W-KIRVRLSA-NH$_2$ (SEQ ID NO: 16) | 32 | >64 | >64 | ND |
| ID17 | H-8-Aoa-QKKIRVRLSA-NH$_2$ (SEQ ID NO: 17) | 64 | >64 | >64 | ND |
| ID18 | (H-W-KKIRVRLSA)$_2$-Lys-β-Ala-NH$_2$ (Core peptide disclosed as SEQ ID NO: 18) | 4 | 32 | 32 | ND |

TABLE 4-continued

MIC values of linear and dimeric peptides and their llpo-derivatives.

| SEQUENCE NAME | Peptide sequence | MIC (ug/mL) | | | |
|---|---|---|---|---|---|
| | | E. coli | P. aeruginosa | K. pneumoniae | S. aureus |
| ID19 | (H-G-W-KIRVRLSA)$_2$-Lys-β-Ala-$NH_2$ (Core peptide disclosed as SEQ ID NO: 19) | 16 | >64 | >64 | ND |
| ID20 | (H-G-QKKIRVRLSA)$_2$-Lys-β-Ala-$NH_2$ (Core peptide disclosed as SEQ ID NO: 20) | 16-32 | >64 | >64 | ND |
| ID21 | (H-5-Ava-W-KKIRVRLSA)$_2$-Lys-β-Ala-$NH_2$ (Core peptide disclosed as SEQ ID NO: 21) | 8-16 | 64 | 64 | ND |
| ID22 | (H-5-Ava-Q-W-KIRVRLSA)$_2$-Lys-β-Ala-$NH_2$ (Core peptide disclosed as SEQ ID NO: 22) | 16 | >64 | >64 | ND |
| ID23 | (H-8-Aoa-OKKIRVRLSA)$_2$-Lys-β-Ala-$NH_2$ (Core peptide disclosed as SEQ ID NO: 23) | 32 | >64 | >64 | ND |
| ID24 | (H-W-KKIRVRLSA)$_2$-Lys-8-Aoa-$NH_2$ (Core peptide disclosed as SEQ ID NO: 24) | 4 | 32 | ND | ND |

ND: not determined

The two compounds ID18 and ID24 resulted the most active. These compounds were tested against a large panel of Gram-negative clinical isolates and the relative MIC values were reported in Table 5 (parts 1-3)

TABLE 5

In vitro activity of ID24 and ID18 vs several clinical isolates of Gram-negative bacteria

| Microorganism | Strain code | MIC (µg/mL) | |
|---|---|---|---|
| | | ID24 | ID18 |
| Acinetobacter baumannii N = 3 | ND000407 | 16 | 16 |
| | ND021408 | 8 | 8 |
| | ND021808 | 8 | 8 |
| | Range | 8-16 | 8-16 |
| Acinetobacter iwoffi | ND033508 | 32 | 16 |
| Enterobacter cloacae N = 4 | ND001607 | 4 | 4 |
| | ND020808 | 16 | 32 |
| | ND029008 | 16 | 32 |
| | ND029408 | 16 | 16 |
| | Range | 4-16 | 4-32 |
| Klebsiella oxytoca N = 2 | ND021308 | 32 | 32 |
| | ND023408 | 16 | 32 |
| | Range | 16-32 | 32 |
| Pseudomonas aeruginosa N = 5 | ATCC10145,L4 | 16 | 16 |
| | ND000207 | 16 | 16 |
| | ND010907 | 8 | 8 |
| | ND033808 | 8 | 8 |
| | ND035408 | 8 | 8 |
| | Range | 8-16 | 8-16 |
| Escherichia coli N = 28 | VECO2526 | 4 | 4 |
| | L47 | 4 | 8 |
| | ND008007 | 8 | 8 |
| | ND020408 | 32 | 32 |
| | ND021608 | 16 | 32 |
| | ND021708 | 8 | 32 |
| | ND022008 | 4 | 8 |
| | ND022108 | 4 | 8 |
| | ND022308 | 4 | 4 |
| | ND022508 | 4 | 4 |
| | ND022608 | 8 | 8 |
| | ND023008 | 8 | 16 |
| | ND023208 | 4 | 2 |
| | ND023808 | 8 | 8 |
| | ND023908 | 4 | 4 |
| | ND027008 | 8 | 8 |
| | ND027408 | 16 | 16 |
| | ND027608 | 16 | 8 |
| | ND027708 | 8 | 8 |
| | ND027808 | 16 | 16 |
| | ND028408 | 8 | 16 |
| | ND028608 | 8 | 8 |
| | ND028808 | 16 | 16 |
| | ND028908 | 16 | 32 |
| | ND029208 | 4 | 2 |
| | ND029508 | 4 | 4 |
| | ND033208 | 16 | 16 |
| | ND034008 | 16 | 16 |
| | Range | 4-32 | 2-32 |
| Proteus mirabilis N = 9 | ND022208 | >128 | >128 |
| | ND022408 | >128 | >128 |
| | ND022808 | >128 | >128 |
| | ND022908 | >128 | >128 |
| | ND023308 | >128 | >128 |
| | ND023508 | >128 | >128 |
| | ND027108 | >128 | >128 |
| | ND027508 | >128 | >128 |
| | ND029108 | >128 | >128 |
| | Range | >128 | >128 |
| Klebsiella pneumoniae N = 17 | ND003407 | 4 | 8 |
| | ND007507 | 8 | 8 |
| | ND020308 | 16 | 16 |
| | ND020507 | 16 | 8 |
| | ND022708 | 4 | 8 |
| | ND023608 | 8 | 16 |
| | ND023708 | 16 | 8 |
| | ND026408 | 8 | 8 |
| | ND027208 | 8 | 8 |
| | ND027308 | 8 | 8 |
| | ND027908 | 4 | 8 |
| | ND028008 | 8 | 8 |
| | ND028108 | 16 | 16 |
| | ND028208 | 8 | 4 |
| | ND028308 | 8 | 8 |
| | ND028508 | 8 | 16 |
| | ND028708 | 8 | 8 |
| | Range | 4-16 | 4-16 |
| Serratia marcescens | ND024008 | >128 | >128 |
| Shigella | ND024108 | 4 | 4 |

TABLE 5-continued

In vitro activity of ID24 and ID18 vs several clinical isolates of Gram-negative bacteria

| Microorganism | Strain code | MIC (µg/mL) | |
| --- | --- | --- | --- |
| | | ID24 | ID18 |
| Stenotrophomonas | ND006507 | 16 | 16 |
| maltophilia | ND021508 | 32 | 32 |
| N = 3 | ND029308 | 8 | 8 |
| | Range | 8-32 | 8-32 |

Cytotoxicity and Haemolysis In Vitro Effects

In Vitro Cytotoxicity

In vitro ID24 cytotoxicity was tested on three cell lines, using the MTT dye reduction assay. The $CC_{50}$ values for ID24 are summarized in Table 6.

TABLE 6

In vitro cytotoxicity of ID24

| Cell line | $CC_{50}$ ID24 (ug/mL) | $CC_{50}$ ID24 (uM) |
| --- | --- | --- |
| HeLa (Human epithelial carcinoma cell line) | 430 | 0.156 |
| HepG2 (Human hepatocellular liver carcinoma cell line) | 215 | 0.078 |
| HaCat (human keratinocyte) | 442.5 | 0.160 |

In Vitro Haemolysis

The haemolysis was determined by two different assays as described in Example VIII. In Tables 7-9 all haemolysis percentage values, determined by UV-VIS spectrophotometry, are reported. In Table 7 in particular, haemolysis percentages of ID24 at different concentrations and in a ratio 1:1 with the erythrocytes suspension are reported. Haemolysis percentages were determined by UV-VIS spectrophotometry, determining the amount of haemoglobin released into the supernatant by reading the absorbance at 414 nm (reference wavelength 490 nm). These results refer to the first method of Example VIII, according to the Shin protocol (Ref. 12).

TABLE 7

Haemolysis percentages of ID24 at different concentrations in an erythrocytes suspension

| | Abs mean* | St. dev. | Haemolysis, % | RSD, % |
| --- | --- | --- | --- | --- |
| Triton 1% | 0.664 | 0.006 | 100.0 | 0.834 |
| Physiological solution | 0.000 | 0.002 | 0.0 | 8.646 |
| ID24 500 ug/mL | 0.090 | 0.008 | 13.6 | 7.232 |
| ID24 250 ug/mL | 0.078 | 0.003 | 11.8 | 2.756 |
| ID24 125 ug/mL | 0.079 | 0.002 | 11.9 | 1.786 |
| ID24 62.5 ug/mL | 0.050 | 0.001 | 7.6 | 1.471 |
| ID24 31.2 ug/mL | 0.037 | 0.005 | 5.6 | 9.024 |

*absorbance value subtracted of blank (physiological solution). Three measurements were carried out for each treatment.

In Table 8, haemolysis percentages of different amounts of ID24 in a 1:1 ratio with whole blood are listed, while in Table 9 haemolysis percentages of different amounts of ID24 in a 1:10 ratio with whole blood are reported. The amount of haemoglobin released into the supernatant was determined by reading the absorbance at 560 nm. These results refer to the second method of Example VIII.

TABLE 8

Haemolysis percentages of ID24 in a ratio 1:1 with whole blood.

| | Abs mean* | St. dev. | Haemolysis, % | RSD, % |
| --- | --- | --- | --- | --- |
| Saponine (1:1) | 1.461 | 0.030 | 100 | 2.003 |
| Physiological solution (1:1) | 0.000 | 0.003 | 0 | 5.623 |
| ID24 1 mg/mL | 0.006 | 0.001 | 0.43 | 1.903 |
| ID24 500 ug/mL | −0.008 | 0.004 | −0.55 | 7.580 |
| ID24 250 ug/mL | −0.008 | 0.002 | −0.55 | 3.297 |
| ID24 125 ug/mL | −0.011 | 0.002 | −0.75 | 3.525 |
| ID24 62.5 ug/mL | −0.013 | 0.003 | −0.89 | 7.777 |

*absorbance value subtracted of blank (physiological solution). Three measurements were carried out for each treatment.

TABLE 9

Haemolysis percentages of ID24 in a ratio 1:10 with whole blood.

| | Abs mean* | St. dev. | Haemolysis % | RSD |
| --- | --- | --- | --- | --- |
| Saponine (1:10) | 2.139 | 0.063 | 100 | 2.872 |
| Physiological solution (1:10) | 0.000 | 0.005 | 0 | 7.588 |
| ID24 (1:10) 500 ug/mL | −0.013 | 0.003 | −0.62 | 4.992 |
| ID24 (1:10) 250 ug/mL | −0.019 | 0.002 | −0.87 | 4.845 |
| ID24 (1:10) 125 ug/mL | −0.013 | 0.006 | −0.61 | 10.986 |
| ID24 (1:10) 62.5 ug/mL | −0.009 | 0.004 | −0.41 | 6.565 |

*absorbance value subtracted of blank (physiological solution). Three measurements were carried out for each treatment.

In Vivo Efficacy in a Septicemia Model in Mice

ID24 was administered intravenously to mice infected intraperitoneally with $7.5 \times 10^2$ CFU of *E. coli* EC47. In particular, ID24 was administered at one dose at 15 min and 6 h post-infection. The results are shown in FIG. 1, which reports a Kaplan-Meier survival curve where ID24 was administered twice, at a dose of 3 mg/kg, at 15 min and 6 hours p.i., while colistin sodium methanesulfonate (CMS) was administered once, at 15 min p.i. at a dose of 3 mg/kg. The mice included in the control group were all dead by the day 3. Each group was made up of 8 mice.

ID24 demonstrated to afford protection of mice from infection caused by a clinical isolate of *E. coli* (EC47).

Antibiofilm Activity

The exposure to different concentrations of ID24 (at ¼, ½, 1, 2 and 4-fold the MIC value) resulted in a substantial reduction of the bacteria biofilm; in the two experiments performed, a percentage of inhibition ranging from 88.7% to 99.9% (from 0.95 to 3.05 log10 of reduction) was observed for all the concentration tested, in comparison with the untreated controls. At subinhibitory concentrations, from 0.9 to 2.35 log10 of reduction was observed at ¼ and ¼-fold the MIC value, respectively.

Figure 2A:
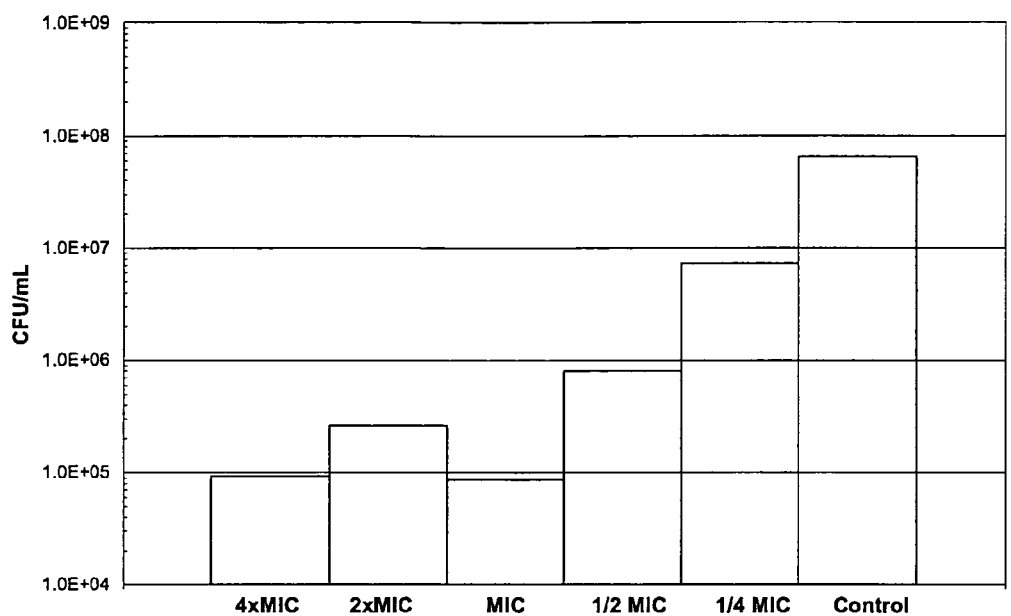
FIG. 2a and FIG. 2b show two histogram plots, where the exposure of a *P. aeruginosa* ATCC 27853 24-hours biofilm to different concentrations of the dimeric peptidic compound ID24 and the reference antibiotic compound CMS, respectively, is reported.
Figure 2B:
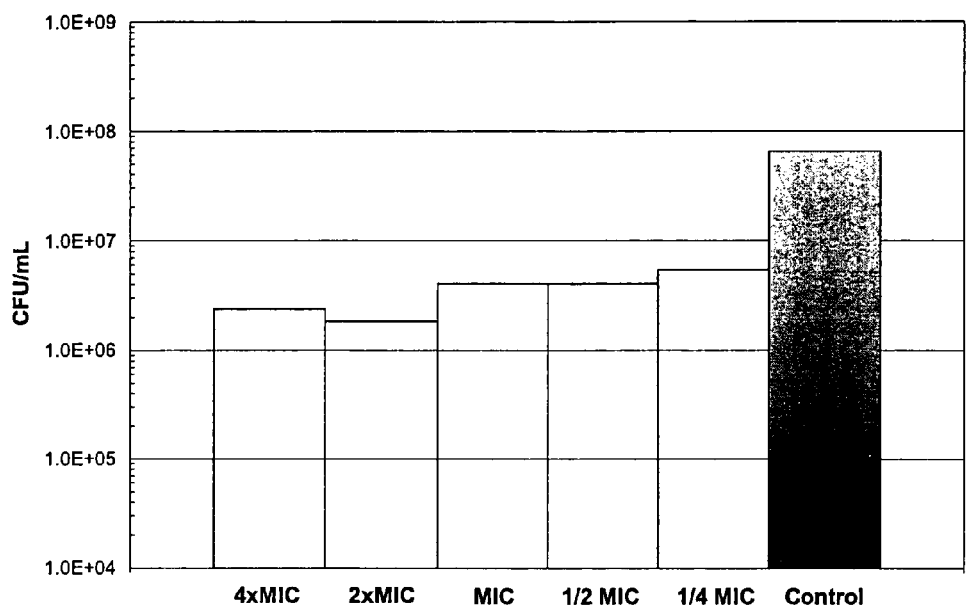

Otherwise colistin resulted less active than ID24; for all the concentration tested, the biofilm reductions were from 88.3% to 97.1% (from 0.88 to 1.55 log10 of CFU/mL of reduction). The results are shown in FIGS. 2a and 2b.

Bibliography

1. J. N. Chin, M. J. Rybak, C. M. Cheung, and P. B. Savage, "Antimicrobial Activities of Ceragenins against Clinical Isolates of Resistant *Staphylococcus aureus*" (2007), *Antimicrobial Agents and Chemotherapy*, 51(4): 1268-1273
2. Y. J, Gordon and E. G. Romanowski, "A Review of Antimicrobial Peptides and Their Therapeutic Potential as Anti-Infective Drugs" (2005), *Current Eye Res.*, 30(7): 505-515.

3. I. S. Radzishevsky, S. Rotem, D. Bourdetsky, S. Navon-Venezia, Y. Carmeli, A. Mor, "Improved antimicrobial peptides based on acyl-lysine oligomers" (2007), *Nature Biotechnology*, 25: 657-659
4. A. K Marra, W. J. Gooderhama and R. E. W. Hancock, "Antibacterial peptides for therapeutic use: obstacles and realistic outlook" (2006), *Current Opinion in Pharmacology*, 6 (5): 468-472.
5. R. E. W. Hancock and R. I. Lehrer, "Cationic peptides: a new source of antibiotics" (1998), *Trends in Biotechnology*, 16 (2): 82-88
6. R. I. Lehrer and T. Ganz, "Antimicrobial peptides in mammalian and insect host defence" (1999), *Current Opinion in Immunology*, 11: 23-27
7. K. Radek and R. Gallo; "Antimicrobial peptides: natural effectors of the innate immune system" (2007), *Seminars in Immunopathology*, 29 (1): 27-43
8. M. G. Scott, H. Yan, and R. E. W. Hancock, "Biological properties of structurally related α-helical cationic antimicrobial peptides" (1999), *Infections and Immunity*, 67 (4): 2005-2009
9. U. H. N. Dürra, U. S. Sudheendraa and A. Ramamoorthy, "LL-37, the only human member of the cathelicidin family of antimicrobial peptides" (2006), *Biochimica at Biophysica Acta-Biomembranes*, 1758 (9): 1408-1425
10. J. L. del Pozo and R. Patel, "The challenge of treating biofilm-associated bacterial infections" (2007), *Clinical Pharmacology and Therapeutics*, 82: 204-209
11. National Committee for Clinical Laboratory Standards. Methods for Dilution Antimicrobial Susceptibility Tests for Bacteria That Grow Aerobically; Approved Standar-Seventh Edition-2006-NCCLS document M7-A7, NCCLS, Wayne, Pa. 2006.
12. S. Y. Shin, J. H. Kang and K.-S. Hahm, "Structure-antibacterial, antitumor and hemolytic activity relationships of cecropin A-magainin 2 and cecropin A-melittin hybrid peptides" (2007), *The Journal of Peptide Research*, 53: 82-90.
13. S. Irwin, "Comprehensive observational assessment: A systematic, quantitative procedure for assessing the behavioral and physiologic state of the mouse" (1968), *Psychopharmacologica*, 13: 222-257

The invention claimed is:

1. A peptidic compound having a length of up to 35 amino acid residues comprising an amino acid sequence represented by the general formula (Ib):

```
Z-[K]n-K-I-R-V-R-L-S-A          (SEQ ID NO: 26)
``` wherein K is a lysine or another amino acid residue with a positively charged side chain, I is an isoleucine, R is an arginine or an amino acid residue with an N-alkyl substituted guanidine side chain, V is a valine, S is a serine, A is an alanine, L is a leucine, wherein one of the amino acid residues K, I, R, L, V and S may be replaced by an alanine, Z is the N-terminal group of the peptidic compound which comprises at least one amino acid residue and is selected from (i) an aromatic amino acid residue or a di-, tri- or tetrapeptidyl group comprising at least one aromatic amino acid residue, wherein the aromatic amino acid residue is particularly selected from tryptophane, N-methyltryptophane, phenylalanine, β-phenylalanine, naphthylalanine, β-naphthylalanine, β-diphenylalanine,β-(4,4'-biphenyl)alanine, β-anthracen-9-ylalanine and β-indol-3-ylalanine, (ii) a branched aliphatic amino acid residue or a di-, tri-, tetrapeptidyl group comprising at least one aliphatic amino acid residue, wherein the aliphatic residue is α-amino acid residue comprising a branched aliphatic side chain of at least 3 C-atoms, (iii) combinations of any one of (i)-(ii), and n is 0 or 1, and wherein the peptidic compound comprises L- and/or D-amino acid residue building blocks, which are selected from α-amino carboxylic acids, β-amino carboxylic acids, or ω-amino carboxylic acids.

2. The peptidic compound according to claim 1, wherein the N-terminal group Z is selected from Ar, Ar-Q, X-Q-Ar, Acetyl-Q-Ar, G-Q-Ar, and pyrE-Ar, wherein Ar is an aromatic amino acid residue, and wherein X is an amino acid residue different from Q.

3. A peptidic compound having the amino acid sequence selected from the group consisting of:

```
WKKIRVRLSA              (SEQ ID NO: 6)

pyrEWKIRVRLSA           (SEQ ID NO: 27)

GQWKIRVRLSA.            (SEQ ID NO: 14)

Acetyl-QWKIRVRLSA       (SEQ ID NO: 12)

Aoa-QWKIRVRLSA          (SEQ ID NO: 16)
and (GQWKIRVRLSA)2 K-β-Ala  (SEQ ID NO: 19)
``` wherein pryE is a pyroglutamic acid residue, Aoa is an 8-amino octanoic acid residue, β-Ala is a β-alanine residue and wherein said peptides are optionally amidated at their C-termini.

4. The peptidic compound according to claim 1, having a length of up to 15 amino acid residues.

5. The peptidic compound according to claim 1, has a linear or cyclic form.

6. A multimeric compound comprising a plurality of said peptidic compound as defined in claim 1.

7. The multimeric compound of claim 6 which is multimerized on a matrix, particularly selected from the group consisting of poly (N-alkyl(meth)acrylamide), poly (N,N-dialkyl (meth)acrylamide), polymelamine, dextrane, cyclodextrine, polyethyleneglycol, and polyvinylpyrrolidone.

8. The multimeric compound of claim 6, wherein said multimetric compound has a branched, particularly a dendritic structure.

9. The multimeric compound of claim 7 selected from the group consisting of:

(i) $R-(Y^1-R)_m-Y^1-(R)_{m'}$  (IIa)

wherein R is a peptidic compound as defined in claim 1, $Y^1$ is a covalent bond or a bifunctional linker, and m is 0 or a positive whole number, and m' is 0 or 1, (ii) $[[(R)_{n1}Y^{1'}]_{n2}]Y^2$  (IIb)

wherein R is a peptidic compound as defined in claim 1, $Y^{1'}$ is in each case independently a linker having a functionality of at least 3, and $Y^2$ is a linker having a functionality of at least 2, and $n_1$ and $n_2$ in each case independently are a whole number of at least 2, and (iii) $\{[[(R)_{n1} Y^{1'}]_{n2}]Y^{2'}\}_{n3}Y^3$  (IIc)

wherein R is a peptidic compound as defined in claim 1, $Y^{1'}$ and $Y^{2'}$ are in each case independent linkers having a functionality of at least 3, $Y^3$ is a linker having a functionality of at least 2, and $n_1$, $n_2$ and $n_3$ are in each case independently whole numbers of at least 2.

10. The multimeric compound of claim 9, wherein said multimeric compound comprises at least one modification selected from the group consisting of a lipid, amide, ester, acyl, and alkyl moiety attached thereto.

11. The multimeric compound of claim 10, comprising at least one lipid moiety comprising at least one amino carboxylic acid comprising a linear or cyclic, saturated mono- or polyunsaturated hydrocarbon group having 3 to 25 C-atoms.

12. The multimeric compound of claim 9 having activity against pathogenic organisms selected from prokaryotic organisms.

13. The multimeric compound of claim 9 having antibacterial activity.

14. A composition for medical use comprising at least one multimeric compound as defined in claim 9 together with pharmaceutically acceptable carriers, diluents, or adjuvants.

15. The composition of claim 1 being in a pharmaceutical dosage form selected from the group consisting of solids, liquids, gels and combinations thereof.

16. A disinfectant or detergent comprising at least one compound as defined in claim 1.

17. A preservative comprising at least one compound as defined in claim 1.

18. The compound of claim 17 as a preservative for medical, cosmetic or food products.

19. The compound of claim 17 for decreasing growth or proliferation of biofilm embedded microorganisms.

20. A veterinary composition comprising at least one peptidic compound as defined in claim 1.

21. A disinfectant or detergent comprising at least one compound as defined in claim 6.

22. A preservative comprising at least one compound as defined in claim 6.

23. A veterinary composition comprising at least one multimeric compound as defined in claim 6.

24. The multimeric compound of claim 9, wherein $Y^1$ is a covalent bond or a bifunctional linker selected from the group consisting of a dialcohol, a dicarboxylic acid, a diamine, an amino acid, a hydroxy carboxylic acid, and a diisocyanate.

25. The multimeric compound of claim 24, wherein the dialcohol is propylene glycol, the dicarboxylic acid is succinic acid, the diamine is ethylene diamine.

26. The multimeric compound of claim 9, wherein $Y^{1'}$ is in each case independently a linker having a functionality of at least 3 which is a trifunctional amino acid selected from the group consisting of lysine, ornithine, nor-lysine, aminoalanine, aspartic acid, and glutamic acid.

27. The multimeric compound of claim 9, wherein $Y^{1'}$ and $Y^{2'}$ are in each case independent linkers having a functionality of at least 3 which is a trifunctional amino acid selected from the group consisting of lysine, ornithine, nor-lysine, aminoalanine, aspartic acid, and glutamic acid.

28. The multimeric compound of claim 11, wherein the at least one amino carboxylic acid is selected from 5-amino valeric acid, 8-amino octanoic acid, and 2-amino decanoic acid.

29. The multimeric compound of claim 11, wherein the at least one amino carboxylic acid is attached to the N- or C-terminus of the multimeric compound.

30. The multimeric compound of claim 1, wherein said amino acid residue K, I, R, L, V or S is an L-amino acid.

* * * * *

UNITED STATES PATENT AND TRADEMARK OFFICE
CERTIFICATE OF CORRECTION

| | |
|---|---|
| PATENT NO. | : 8,785,399 B2 |
| APPLICATION NO. | : 12/995802 |
| DATED | : July 22, 2014 |
| INVENTOR(S) | : Andreaw Giuliani et al. |

Page 1 of 1

It is certified that error appears in the above-identified patent and that said Letters Patent is hereby corrected as shown below:

On the title page, "(73) Assignee:", delete "S.R.A." and insert --S.R.L.--.

Signed and Sealed this
Fourteenth Day of October, 2014

Michelle K. Lee
*Deputy Director of the United States Patent and Trademark Office*

```
SEQUENCE LISTING

<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      antibacterial peptide

<400> SEQUENCE: 1

Gln Lys Lys Ile Arg Val Arg Leu Ser Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 2

Phe Lys Lys Ile Arg Val Arg Leu Ser Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 3

Ile Lys Lys Ile Arg Val Arg Leu Ser Ala
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide
```

<400> SEQUENCE: 4

Leu Lys Lys Ile Arg Val Arg Leu Ser Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 5

Val Lys Lys Ile Arg Val Arg Leu Ser Ala
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 6

Trp Lys Lys Ile Arg Val Arg Leu Ser Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 7

Tyr Lys Lys Ile Arg Val Arg Leu Ser Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 8

Gln Phe Lys Ile Arg Val Arg Leu Ser Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 9

Gln Ile Lys Ile Arg Val Arg Leu Ser Ala
1               5                   10

<210> SEQ ID NO 10
<211> LENGTH: 10

```
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 10

Gln Leu Lys Ile Arg Val Arg Leu Ser Ala
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 11

Gln Val Lys Ile Arg Val Arg Leu Ser Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 12

Gln Trp Lys Ile Arg Val Arg Leu Ser Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      minilibrary peptide

<400> SEQUENCE: 13

Gln Tyr Lys Ile Arg Val Arg Leu Ser Ala
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      linear peptide

<400> SEQUENCE: 14

Gly Gln Trp Lys Ile Arg Val Arg Leu Ser Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid
```

<400> SEQUENCE: 15

Xaa Trp Lys Lys Ile Arg Val Arg Leu Ser Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid

<400> SEQUENCE: 16

Xaa Gln Trp Lys Ile Arg Val Arg Leu Ser Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-aminooctanoic acid

<400> SEQUENCE: 17

Xaa Gln Lys Lys Ile Arg Val Arg Leu Ser Ala
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Branched sequence
<220> FEATURE:
<221> NAME/KEY: MOD_RES
<222> LOCATION: (12)..(12)
<223> OTHER INFORMATION: Beta-Ala

<400> SEQUENCE: 18

Trp Lys Lys Ile Arg Val Arg Leu Ser Ala Lys Ala
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: Branched sequence
<220> FEATURE:
<221> NAME/KEY: MOD_RES
<222> LOCATION: (13)..(13)

```
<223> OTHER INFORMATION: Beta-Ala

<400> SEQUENCE: 19

Gly Gln Trp Lys Ile Arg Val Arg Leu Ser Ala Lys Ala
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: Branched sequence
<220> FEATURE:
<221> NAME/KEY: MOD_RES
<222> LOCATION: (13)..(13)
<223> OTHER INFORMATION: Beta-Ala

<400> SEQUENCE: 20

Gly Gln Lys Lys Ile Arg Val Arg Leu Ser Ala Lys Ala
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: Branched sequence
<220> FEATURE:
<221> NAME/KEY: MOD_RES
<222> LOCATION: (1)..(1)
<223> OTHER INFORMATION: 5-aminovaleric acid
<220> FEATURE:
<221> NAME/KEY: MOD_RES
<222> LOCATION: (13)..(13)
<223> OTHER INFORMATION: Beta-Ala

<400> SEQUENCE: 21

Xaa Trp Lys Lys Ile Arg Val Arg Leu Ser Ala Lys Ala
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: Branched sequence
<220> FEATURE:
<221> NAME/KEY: MOD_RES
<222> LOCATION: (1)..(1)
<223> OTHER INFORMATION: 5-aminovaleric acid
<220> FEATURE:
<221> NAME/KEY: MOD_RES
<222> LOCATION: (13)..(13)
<223> OTHER INFORMATION: Beta-Ala

<400> SEQUENCE: 22

Xaa Gln Trp Lys Ile Arg Val Arg Leu Ser Ala Lys Ala
```

```
<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: Branched sequence
<220> FEATURE:
<221> NAME/KEY: MOD_RES
<222> LOCATION: (1)..(1)
<223> OTHER INFORMATION: 8-aminooctanoic acid
<220> FEATURE:
<221> NAME/KEY: MOD_RES
<222> LOCATION: (13)..(13)
<223> OTHER INFORMATION: Beta-Ala

<400> SEQUENCE: 23

Xaa Gln Lys Lys Ile Arg Val Arg Leu Ser Ala Lys Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: Branched sequence
<220> FEATURE:
<221> NAME/KEY: MOD_RES
<222> LOCATION: (12)..(12)
<223> OTHER INFORMATION: 8-aminooctanoic acid

<400> SEQUENCE: 24

Trp Lys Lys Ile Arg Val Arg Leu Ser Ala Lys Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid
<220> FEATURE:
<221> NAME/KEY: misc_feature
<222> LOCATION: (1)..(4)
<223> OTHER INFORMATION: This region may encompass 1-4 residues wherein
      some positions may be absent
<220> FEATURE:
<221> NAME/KEY: MOD_RES
<222> LOCATION: (5)..(5)
<223> OTHER INFORMATION: Any amino acid with a lysine side chain or any
      amino acid with a positively charged side chain or any amino acid
      with an alanine side chain
<220> FEATURE:
<221> NAME/KEY: misc_feature
<222> LOCATION: (5)..(5)
<223> OTHER INFORMATION: This position may or may not be present
<220> FEATURE:
<221> NAME/KEY: MOD_RES
```

```
<222> LOCATION: (6)..(6)
<223> OTHER INFORMATION: Any amino acid with a lysine side chain or any
      amino acid with a positively charged side chain or any amino acid
      with an alanine side chain
<220> FEATURE:
<221> NAME/KEY: MOD_RES
<222> LOCATION: (7)..(7)
<223> OTHER INFORMATION: Any amino acid with an isoleucine side chain or
      any amino acid with an alanine side chain
<220> FEATURE:
<221> NAME/KEY: MOD_RES
<222> LOCATION: (8)..(8)
<223> OTHER INFORMATION: Any amino acid with an arginine side chain or
      an N-alkyl substituted guanidine side chain or any amino acid with
      an alanine side chain
<220> FEATURE:
<221> NAME/KEY: MOD_RES
<222> LOCATION: (9)..(9)
<223> OTHER INFORMATION: Any amino acid with a valine side chain or any
      amino acid with an alanine side chain
<220> FEATURE:
<221> NAME/KEY: MOD_RES
<222> LOCATION: (10)..(10)
<223> OTHER INFORMATION: Any amino acid with an arginine side chain or
      an N-alkyl substituted guanidine side chain or any amino acid with
      an alanine side chain
<220> FEATURE:
<223> OTHER INFORMATION: See specification as filed for detailed
      description of substitutions and preferred embodiments

<400> SEQUENCE: 25

Xaa Xaa Xaa Xaa Xaa Xaa Xaa Xaa Xaa Xaa
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid
<220> FEATURE:
<221> NAME/KEY: misc_feature
<222> LOCATION: (1)..(4)
<223> OTHER INFORMATION: This region may encompass 1-4 residues wherein
      some positions may be absent
<220> FEATURE:
<221> NAME/KEY: MOD_RES
<222> LOCATION: (5)..(5)
<223> OTHER INFORMATION: Any amino acid with a lysine side chain or any
      amino acid with a positively charged side chain or any amino acid
      with an alanine side chain
<220> FEATURE:
<221> NAME/KEY: misc_feature
<222> LOCATION: (5)..(5)
<223> OTHER INFORMATION: This position may or may not be present
<220> FEATURE:
<221> NAME/KEY: MOD_RES
<222> LOCATION: (6)..(6)
<223> OTHER INFORMATION: Any amino acid with a lysine side chain or any
      amino acid with a positively charged side chain or any amino acid
      with an alanine side chain
<220> FEATURE:
<221> NAME/KEY: MOD_RES
<222> LOCATION: (7)..(7)
<223> OTHER INFORMATION: Any amino acid with an isoleucine side chain or
      any amino acid with an alanine side chain
<220> FEATURE:
<221> NAME/KEY: MOD_RES
<222> LOCATION: (8)..(8)
<223> OTHER INFORMATION: Any amino acid with an arginine side chain or
      an N-alkyl substituted guanidine side chain or any amino acid with
      an alanine side chain
```

```
<220> FEATURE:
<221> NAME/KEY: MOD_RES
<222> LOCATION: (9)..(9)
<223> OTHER INFORMATION: Any amino acid with a valine side chain or any
      amino acid with an alanine side chain
<220> FEATURE:
<221> NAME/KEY: MOD_RES
<222> LOCATION: (10)..(10)
<223> OTHER INFORMATION: Any amino acid with an arginine side chain or
      an N-alkyl substituted guanidine side chain or any amino acid with
      an alanine side chain
<220> FEATURE:
<221> NAME/KEY: MOD_RES
<222> LOCATION: (11)..(11)
<223> OTHER INFORMATION: Any amino acid with a leucine side chain or any
      amino acid with an alanine side chain
<220> FEATURE:
<221> NAME/KEY: MOD_RES
<222> LOCATION: (12)..(12)
<223> OTHER INFORMATION: Any amino acid with a serine side chain or any
      amino acid with an alanine side chain
<220> FEATURE:
<221> NAME/KEY: MOD_RES
<222> LOCATION: (13)..(13)
<223> OTHER INFORMATION: Any amino acid with an alanine side chain
<220> FEATURE:
<223> OTHER INFORMATION: See specification as filed for detailed
      description of substitutions and preferred embodiments

<400> SEQUENCE: 26

Xaa Xaa Xaa Xaa Xaa Xaa Xaa Xaa Xaa Xaa Xaa Xaa Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid

<400> SEQUENCE: 27

Glu Trp Lys Ile Arg Val Arg Leu Ser Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Ile, Leu, Val, Trp or Tyr

<400> SEQUENCE: 28

Xaa Lys Lys Ile Arg Val Arg Leu Ser Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Phe, Ile, Leu, Val, Trp or Tyr

<400> SEQUENCE: 29

Gln Xaa Lys Ile Arg Val Arg Leu Ser Ala
1               5                   10
```